United States Patent [19]

Ithakissios

[11] 4,115,534
[45] Sep. 19, 1978

[54] IN VITRO DIAGNOSTIC TEST

[75] Inventor: Dionyssis S. Ithakissios, St. Paul, Minn.

[73] Assignee: Minnesota Mining and Manufacturing Company, St. Paul, Minn.

[21] Appl. No.: 808,339

[22] Filed: Jun. 20, 1977

Related U.S. Application Data

[63] Continuation-in-part of Ser. No. 715,933, Aug. 19, 1976, abandoned.

[51] Int. Cl.² ............... G01N 33/16; A61K 43/00
[52] U.S. Cl. .................... 424/1; 252/62.53; 252/316; 23/230 B
[58] Field of Search ............ 252/316, 62.53, 301.1 R; 424/1, 19, 36, 64; 23/230 B

[56] References Cited

U.S. PATENT DOCUMENTS

| 650,760 | 5/1900 | Metcalf | 424/94 X |
|---|---|---|---|
| 2,971,916 | 2/1961 | Schleicher et al. | 252/62.53 |
| 3,137,631 | 6/1964 | Soloway | 424/36 X |
| 3,522,346 | 7/1970 | Chang | 252/316 X |
| 3,933,997 | 1/1976 | Hersh et al. | 424/1 |
| 3,970,518 | 7/1976 | Giaever | 23/230 B |
| 3,980,764 | 9/1976 | Adams | 424/1 |

*Primary Examiner*—Benjamin R. Padgett
*Assistant Examiner*—Christine M. Nucker
*Attorney, Agent, or Firm*—C. Alexander; Donald M. Sell; James V. Lilly

[57] ABSTRACT

A method for determining the concentration of substances in biological fluids (e.g., drugs, hormones, vitamins and enzymes) is disclosed wherein magnetically responsive, permeable, solid, water-insoluble microparticles are employed.

25 Claims, 2 Drawing Figures

FIG. 1

FIG. 2

IN VITRO DIAGNOSTIC TEST

CROSS REFERENCE TO RELATED APPLICATION

This is a continuation-in-part of copending application Ser. No. 715,933, filed August 19, 1976, abandoned.

BACKGROUND OF THE INVENTION

This invention relates to methods for determining the concentration of substances in biological fluids. More particularly it relates to such methods wherein magnetically responsive composite microparticles having a permeable, solid, water-insoluble matrix comprising a proteinaceous material, a polysaccharide, a polyurethane or mixtures thereof are employed.

Techniques useful in determining concentrations of substances in biological fluids, such as serum or urine, are known. The most common of these techniques are in vitro assay procedures. Frequently they involve competitive binding of the substance whose concentration is to be determined, and a radioactively labeled analog thereof, to binding sites on a specific receptor (usually a protein or antibody). The portion of the substance bound to the receptor is then separated from the portion not bound to the receptor and counted for radioactivity. The concentration of the substance is then determined by comparing the counted radioactivity with a standard curve.

Techniques employed to separate the bound from the unbound fractions include, for example, differential migration of the bound and free fractions (e.g., by electrophoresis, chromatoelectrophoresis, gel filtration, etc.); chemical precipitation of the bound or free fraction (e.g., by means of organic solvents, salts, acids, etc.); immunological precipitation of the bound fraction (e.g., by the double antibody method); adsorption of the bound or free fraction onto selective sorbing media (e.g., charcoal, silicates, resins, etc.).

Some of these techniques require rather complicated procedures in order to bring about separation of the bound from the free fractions. Such procedures reduce operator efficiency and increase the cost of the tests. As a result they are not suited to large scale operations. Other of these techniques do not adequately distinguish between the bound and free fractions and therefore lack the accuracy preferred in in vitro testing. Still other of these techniques can only be utilized in a limited number of tests.

Recently attempts have been made to simplify in vitro testing for substances present in biological fluids. For example, U.S. Pat. No. 3,933,997 discloses a process and composition useful in determining concentrations of digoxin in body fluids. The composition consists of anti-digoxin antibodies covalently bonded to an intermediate silane which is in turn coupled to magnetically responsive particles. The particles can be magnetically separated from a test solution.

Antibodies used in such composition are, therefore, coupled to the surface of the particles thereby limiting the amount of antibody present thereon. This has the further effect of limiting the binding capacity of the compositions. Additionally, when such compositions are prepared from anti-sera having low titer certain particles may not have any antibody bound thereto. Additionally, the process of covalently bonding the antibody to the intermediate silane must be carefully controlled so that the complexing ability is not lost. Moreover, this composition is only useful in determining concentrations of digoxin.

U.S. Pat. No. 3,970,518 discloses small magnetic particles whose surface is coated with a layer of antibody. Such coated magnetic particles are useful in sorting out and separating tiny select viruses, bacteria and other cells from multi-cell, bacteria or virus populations. The amount of antibody in such compositions available for sorting and separating is also limited by the available external surface area of the magnetic material.

The process of the present invention overcomes these deficiencies of the prior art. It employs compositions wherein the permeable, solid, water-insoluble matrix of the microparticle itself is capable of sorbing substances present in biological fluids (e.g., drugs, hormones, vitamins, proteins, enzymes). Additionally, the sorptive properties of the microparticles useful in the process of the invention are not lost during their preparation. Still further, the microparticles useful in the process of the present invention have a substantially greater binding capacity than do compositions employed in prior art processes. This is because the microparticles useful in the present invention are permeable thereby allowing biological fluids to penetrate into the interior of the particle and be sorbed therein. As a result the binding capacity of particles useful in the present invention is not limited by the amount of the external surface area of the particle. As a result the process of the present invention provides a more accurate diagnostic test than do prior art processes. Furthermore, the process of the present invention is useful in a wide variety of in vitro diagnostic tests.

The process of the present invention is, therefore, useful in determining the concentration of a variety of substances in biological fluids in a rapid, efficient and accurate manner. Thus it may be employed to measure the amount of drugs (e.g., digoxin and antibiotics), hormones (e.g., thyroxine), vitamines (e.g., vitamin $B_{12}$), proteins, enzymes, etc. Because the particles useful in the invention are magnetically responsive they are rapidly and efficiently separable from the test solution. Thus the process is simple to use and eliminates the necessity to employ complicated and expensive separation techniques. Consequently it is particularly useful in large scale testing wherein a number of separate samples are tested at the same time. Moreover, the process of the invention may be designed to test for a specific substance or a variety of substances.

SUMMARY OF THE INVENTION

In accordance with the present invention there is provided a method for determining the concentration of substances present in biological fluids wherein magnetically responsive composite microparticles comprising a magnetically responsive material and a permeable, solid, water-insoluble matrix selected from proteinaceous materials, polysaccharides, polyurethanes and mixtures thereof are competitively reacted with the substance and a radioactively labeled form of the substance. The microparticles are then separated, counted for radioactivity and the concentration of the substance determined by comparison of the count with a standard curve.

The matrix of the microparticles is capable of sorbing substances present in biological fluids. The matrix may itself sorb the particular substance under test or it may contain a combining agent which sorbs the substance. In either event, the sorption may be general, that is the matrix or combining agent may be capable of sorbing a number of substances, or it may be specific, that is the matrix or combining agent may be capable of sorbing only a particular substance.

As it is used herein, the term "sorb" means "to collect one material either (i) on the surface of, or (ii) within the body of a second material". Thus the term "sorb" includes adsorb and absorb; the term "sorbent" includes adsorbent and absorbent; the term "sorption" includes adsorption and absorption.

BRIEF DESCRIPTION OF THE DRAWINGS

The present invention is described in more detail hereinafter with reference to the accompanying drawings in which the same reference number refers to the same elements throughout the several views and in which.

DETAILED DESCRIPTION OF THE INVENTION

As previously stated, the process of the present invention is useful in determining concentrations of drugs, hormones, vitamins, proteins, enzymes, etc. present in biological fluids. While the process may be carried out by a variety of techniques, one of the following two procedures is commonly used. In the first, predetermined amounts of the following ingredients are employed:

(a) a biological fluid containing the substance whose concentration is to be measured;
(b) a radioactively labeled form of that substance; and
(c) composite microparticles of the invention wherein a combining agent which specifically sorbs the substance is included within the matrix, or wherein the matrix itself specifically sorbs the substance.

The ingredients are reacted so as to cause the substance whose concentration is to be determined and its labeled form to competitively complex with the available sites on the microparticles. The resultant complexed microparticles are then magnetically separated from the reaction solution and the radioactivity of either the composite microparticles or the remaining reaction solution counted. The concentration of the substance to be measured is then determined by comparing the counted radioactivity with a standard curve.

The exact amounts of the labeled form of the substance and the magnetically responsive microparticles used in this process are selected so that there is an excess of the labeled substance over the total number of sites available for complexing on the microparticles. This insures that the labeled and unlabeled forms of the substance will compete for the sites.

In the second process, predetermined amounts of the following ingredients are employed:

(a) a biological fluid containing the substance whose concentration is to be measured;
(b) a radioactively labeled form of that substance;
(c) a specific binding agent for the substance; and
(d) composite microparticles of the invention containing a combining agent in the matrix which is a general sorbent or where the matrix itself acts as a general sorbent.

Ingredients (a), (b) and (c) are reacted to cause the substance and its labeled form to competitively bind to the available binding agent. The microparticles (d) are then added to, and reacted with, the mixture so as to cause that portion of both the substance and its labeled form not bound to the binding agent (that is, the free forms thereof) to complex with the available sites on the microparticles. The resultant complexed microparticles are then magnetically separated and the concentration of the substance determined as described above.

In this method the amount of specific binding agent should be selected so that neither all of the substance or its labeled form becomes bound thereto. The quantity of microparticles employed should be selected so that substantially all of the free portions of the substance and its labeled form complex therewith. Thus, the quantity of the microparticles should provide more sites for complexing than there is free substance and free labeled substance.

The reactions employed in these methods are generally carried out at room temperature (e.g., 20°–25° C.) in a short time (e.g., 10–30 minutes). Preferably, they are carried out with agitation.

Frequently, the substance whose concentration is to be determined is attached to or combined with other materials in the test sample. Such attached or combined substances, also referred to as endogenous substances, are preferably liberated from these materials so as to improve the accuracy of the assay. Various techniques for liberation may be employed and are well known to those in the art. Thus, for example, thermal or chemical techniques may be employed.

Various techniques may be employed in order to separate the microparticles of the invention from the test sample. For example, they may be separated by placing a permanent magnet in close proximity to the vessel containing the test sample and then decanting the liquid portion thereof. Alternatively, an electromagnet may be employed in place of the permanent magnet. Special devices for quickly, easily and automatically causing the separation of the magnetic microparticles from the sample may be employed.

Figure 1:
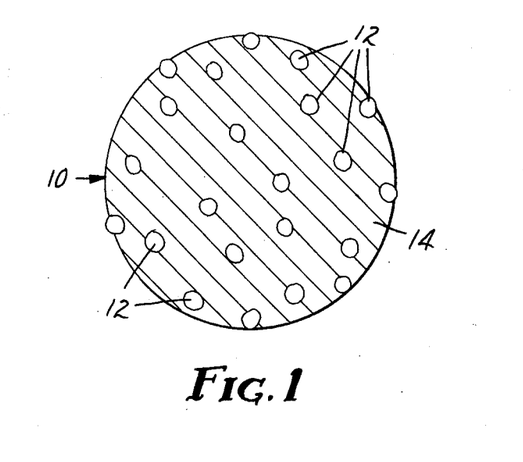
FIG. 1 is a cross-sectional view of one type of microparticle useful in the process of the invention.
Figure 2:
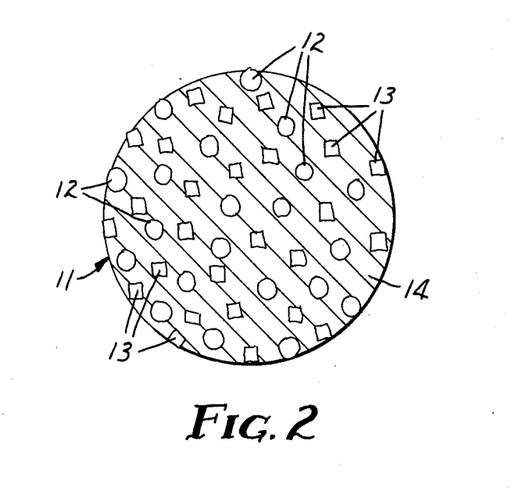
FIG. 2 is a cross-sectional view of an alternative microparticle useful in the process of the present invention.

Microparticles useful in the present invention are shown in FIGS. 1 and 2. Referring now specifically to FIG. 1 there is shown a cross-sectional view of one type of composite microparticle 10 useful in the invention. This microparticle comprises a magnetically responsive material 12 dispersed throughout a permeable, solid, water-insoluble proteinaceous matrix 14. The magnetically responsive material 12 is typically uniformly dispersed throughout the microparticle. Additionally some of the magnetically responsive material projects from the surface of the microparticle so as to be partially exposed in the figures.

FIG. 2 shows a cross-sectional view of a composite microparticle 11 also useful in the present invention. Composite microparticle 11 comprises a magnetically responsive material 12 and a combining agent 13 each of which are dispersed throughout a permeable, solid, water-insoluble proteinaceous matrix 14. The combining agent 13 is typically uniformly dispersed throughout the microparticle. Additionally some of the combining agent projects from the exterior surface of the microparticle so as to be partially exposed.

The indicia employed to represent magnetically responsive material 12 and combining agent 13 are intended for illustrative purposes only and are not meant to limit the microparticles useful in the invention. More- over, the shape of the magnetically responsive material 12 and combining agent 13 is not critical to the practice of the invention.

Suitable magnetically responsive materials for use in the microparticles are water-insoluble. Additionally, it is preferred they have a high magnetic permeability so that the field of the magnet used to separate the composites will be "focused" therein, thereby allowing rapid and thorough retrieval of the particles.

The quantity of magnetically responsive material present in the microparticles may be varied. Preferably it comprises from about 5 to 75 percent by weight of the microparticles. Most preferably it comprises from about 45 to 75 percent by weight of the microparticles.

Representative examples of useful magnetically responsive materials include ferromagnetic substances such as the metallic oxides (e.g., $BaFe_{12}O_{19}$, $Fe_3O_4$, CoO, NiO, $Mn_2O_3$), iron and nickel particles, etc. Another useful ferromagnetic material is CoMnP.

Matrices suitable for use in the microparticles may be prepared from proteinaceous materials, polysaccharides, polyurethanes and mixtures thereof. The proteinaceous materials may be either naturally occurring (e.g., albumins) or synthetic (e.g., synthetic polypeptides). In either event they are polymers which are primarily comprised of carbon, hydrogen, oxygen, sulfur and nitrogen and which have the general formula Their molecular weights may range from a few thousand to several hundred thousand. They may be used singly or in combination in preparing the matrix.

Representative examples of useful natural proteinaceous materials include albumin, gelatin, globulins (e.g., antibodies) and enzymes. Representative examples of useful polypeptides include polylysine and polyglutamic acid.

Representative examples of useful polysaccharides include starch, acacia, gum ghatti, gum xanthan, gum karaya, gum tragacanth, carragheenan, pectin and polygalacturonic acid, glycogen, dextran or cellulose.

Polyurethanes useful in the present invention are typically prepared by the reaction of polyfunctional isocyanate materials (e.g., isocyanate functionality of more than one) with polyol, polyester or polyether materials which have reactive hydroxyl groups. Prereacted isocyanate-terminated prepolymers are also useful in preparing the polyurethanes.

Preferably the polyurethane matrix is derived from an isocyanate-terminated polyester prepolymer. The prepolymer may be prepared by reacting a polyfunctional isocyanate with a polyester. A commercially available isocyanate-terminated polyester suitable for use in the present invention is "Formrez P611" (a waxy thermoplastic solid at room temperature having an isocyanate equivalent weight of 627–667, that is its gram molecular weight per isocyanate group is 627–667, and having an available isocyanate content of 5.8 to 6.4 percent, commercially available from Witco Chemical Company).

Polyfunctional isocyanates useful in preparing the polyurethane include monomeric and polymeric aliphatic and aromatic isocyanates. Representative examples of such isocyanates include 4,4'-diphenyl methane diisocyanate; 2,4-toluene diisocyanate; 2,6-toluene diisocyanate; 4,4'-methylene bis(cyclohexyl)isocyanate; etc.

Suitable polyesters include those prepared by the reaction of a glycol (e.g., ethylene or propylene glycol) with a dicarboxylic acid (e.g., terephthalic, isophthalic and sebacic acids).

When used in determining concentrations of substances present in biological fluids, the matrix of the microparticles may itself sorb the substances or, alternatively, it may contain a combining agent which sorbs the substances.

Combining agents useful in the microparticles are those materials which join with substances present in biological fluids. The exact mechanism by which these agents join with such substances is not completely understood. However, it is believed that some of such agents react with oppositely charged groups on the substance whose concentration is being determined, while others are believed to form covalent bonds with the substance. It is also believed that still others form bonds with the substance through van der Waals forces, hydrogen bonds, etc.

In any event, the combining agents useful in the present invention include general sorbents for the substance (e.g., granulated charcoal and ion-exchange resins) and specific sorbents for the substance (e.g., throxine antibody for T-4 or fish serum, such as sockeye salmon serum, oyster toadfish serum and rainbow trout serum, or intrinsic factor for vitamin $B_{12}$). Granulated charcoal is useful when the concentration of vitamin $B_{12}$ is to be determined. Ion-exchange resins of the anionic variety are useful when the concentration of thyroxine (T-4) is to be determined.

Ion-exchange resins may be broadly categorized as insoluble acids or bases which remain insoluble when converted to salts. They contain fixed electronegative or electropositive charges. Thus, cation-exchange resins are those which contain fixed electronegative charges, while anion-exchange resins are those which contain fixed electropositive charges.

Ion-exchange resins may be organic or inorganic solids or liquids. Preferably they are organic polymers. They may be classified as strong-acid and weak-base materials. Each of the ion-exchange resins have active groups associated therewith. Representative examples of these active groups are sulfonic, carboxylic and phosphonic acid groups; quaternary ammonium groups and secondary and tertiary amine groups.

Commonly used polymeric ion-exchange resins are based upon crosslinked polystyrene (e.g., sulfonated copolymers of styrene and divinylbenzene). Quaternary ammonium derivatives of this copolymer provide strong-base anion-exchange resins while secondary and tertiary amine derivatives provide weakbase anion-exchange resins.

Other useful ion-exchange resins include copolymers of (i) acrylic and methacrylic acids or esters or the corresponding nitriles and (ii) the condensation product of epichlorohydrin with amines.

The above-described ion-exchange resins are further discussed in *Encyclopedia of Polymer Science and Technology*, Vol. 7, Interscience Publishers, 1967, pages 692–723, incorporated herein by reference.

Representative examples of commercially available ion-exchange resins of the type described above include "Dowex 1" and "Dowex 2" (crosslinked polystyrene-quaternary ammonium resin available from Dow Chemical Co.); "Amberlite 400" (crosslinked polystyrene-quaternary ammonium resin available from Rohm and Haas Company). Other examples of useful commercially available ion-exchange resins maybe found in the *Encyclopedia of Polymer Science and Technology*, Vol. 7, Interscience Publishers, 1967, at pages 696–698.

Still other useful ion-exchange resins include those disclosed in U.S. Pat. No. 3,702,821. These resins comprise crosslinked polystyrene-quaternary ammonium resin treated with a chelating agent. Useful chelating agents include hydroxy and carboxylic acids, inorganic anions which have sequestering properties such as fluoride and phosphate, etc.

The amount of combining agent employed in the matrix is not critical to the process of the present invention provided that there is sufficient agent present to join with the substance whose concentration is being measured. Thus the amount is primarily dependent upon the agent used and the substance whose concentration is to be determined.

Composite microparticles useful in the present invention may be conveniently prepared. Usually the particles are spherical although it is not necessary that they be so. In any event, their surfaces may be either substantially smooth (e.g., having no major irregularities therein) or rough (e.g., having numerous cavities therein). The size of the particles employed in the process of the present invention is not critical, it being understood that, for a given mass of microparticles, the surface area increases as the diameter of the particles decreases. In any event, the maximum dimension of the particles may vary over a wide range. Typically their maximum dimension is in the range of about 5 to 400 microns. Preferably it is in the range of about 10 to 250 microns.

Composite particles having a matrix derived from proteinaceous or polysaccharide material (no combining agent being present) may be made by mixing the magnetically responsive material with an aqueous solution of a matrix-forming material and injecting the mixture through a hypodermic needle into a heated and vigorously stirred bath liquid with which the mixture is incompatible, such as a bath of vegetable oil, to form microparticles which are crosslinked by the heat and thereby made water-insoluble. The resulting particles may then be collected and purified by filtering the bath and washing the filtrate with organic solvents (e.g., heptane) and water. Other ingredients such as diluents may also be included in the mixture prior to its injection into the bath.

Alternatively, they may be prepared by dispersing a mixture of magnetically responsive material and matrix-forming material in a vigorously stirred bath of a liquid with which the mixture is incompatible (e.g., vegetable oil), heating to drive off water, collecting the resultant microparticles (e.g., by filtration) and heating the collected microparticles until they are insolubilized.

In an alternative and preferred process the composites may be prepared by a room temperature technique by injecting a mixture of magnetically responsive material, aqueous solution of proteinaceous material, and combining agent, if present, into a stirred bath of vegetable oil containing a lipophilic drying agent and a crosslinking agent. The dispersion is preferably maintained for about two hours during which time the dispersed droplets are dehydrated and proteinaceous material in the dispersed phase is crosslinked. The resultant water-insoluble composite microparticles may then be collected and purified as described above. This process is useful when it is desired that the matrix have specific sorptive properties or when the matrix contains a combining agent.

Suitable lipophilic drying agents include aliphatic alcohols such as n-butanol, 2-ethylhexanol, etc. The amount of drying agent employed is not critical to the invention provided that a sufficient amount is used so as to dissolve substantially all of the water present in the reaction solution.

Suitable crosslinking agents include aldehydes such as formaldehyde and glutaric dialdehyde. Although the amount of crosslinking agent employed may vary, it is preferred that it comprise from about 2 to 5 parts by weight of the proteinaceous material to be crosslinked.

Despite being crosslinked and rendered water-insoluble during preparation of the microparticles, the proteinaceous and polysaccharide materials, whether present as matrix material or combining agent, retain sufficient activity to sorb substances in biological fluids. Moreover, the microparticles retain their permeability despite being crosslinked. Thus they increase in size (e.g., swell) when employed in the process of the invention without dissolving.

In another alternative process composites of the invention which have a polyurethane matrix, and optionally combining agent, may be prepared by injecting a mixture of the polyurethane reactants and magnetically responsive material into a vigorously stirred aqueous phase which preferably contains a surfactant to form microparticles. The microparticles are crosslinked and made water-insoluble by heating. The resulting particles may be filtered, washed with water and dried.

The particle size range of the microparticles can be controlled by varying either or both the rate of injection and the degree of agitation. Moreover, the addition of small amounts of surfactants (e.g., 0.1–2 percent by weight of the injected solution) also influences the size of the microparticles.

Once prepared the microparticles are preferably formed into tablets by techniques known to the art. An excipient, or combination thereof, is employed to maintain the integrity of the tablet. Excipients employed should not affect either the sorbtive properties of the matrix or the results of the assay. Additionally it is preferred that they permit the tablet to rapidly dissolve and disperse in test solutions. Once prepared the tablets are exposed to a strong magnetic field for about one second so as to magnetize them. However, once dispersed, the microparticles do not substantially reagglomerate until subjected to an external magnetic field.

The magnetized tablets are especially convenient to use in the present invention because they contain a predetermined amount of the microparticles. Thus, the need to weigh the microparticles prior to addition to the test solution is eliminated.

Tablets comprising about 10 to 30 percent by weight composite microparticles and, correspondingly, 80 to 70 percent by weight excipient are preferred.

Excipients useful in the tablets include lactose (U.S.P.), corn starch (U.S.P.), unmilled dicalcium phosphate (N.F.), microcrystalline cellulose (N.F.), etc.

The following examples further illustrate without limiting the present invention.

EXAMPLE 1

Magnetically responsive composite microparticles having magnetically responsive material dispersed throughout a permeable, solid, crosslinked, water-insoluble protein matrix were prepared. An aqueous mixture comprising 0.5 gram (g) magnetically responsive material ($BaFe_{12}O_{19}$) in 1.5 milliliter (ml) protein solution (bovine serum albumin in water, 0.35 g/ml) was added dropwise into a rapidly stirred continuous phase comprising 200 ml dewatering agent (n-butanol), 2.4 ml crosslinking agent (formaldehyde, 35 percent by weight in water) and 200 ml oil (castor oil) to produce a dispersion of the aqueous mixture in the continuous phase. The dispersion was mixed for 2 hours at room temperature (e.g., 20°-25° C.) to crosslink the protein matrix. The resulting solid microparticles are collected by vacuum filtration. Residual oil was removed by contacting the microparticles with n-heptane in a Soxhlet extractor for about 18 hours. Residual water-soluble components were then removed in a similar manner by contacting the microparticles with water in the Soxhlet extractor for about 10 hours. The microparticles were then dried at 80° C. for 24 hours. The dried microparticles were spherical and approximately 90 percent had diameters in the range of about 10 to 100 microns.

The microparticles were used in a thyroxine (T-4) radioassay as follows:

Separate mixtures each comprising 2 ml hydrochloric acid (0.05 molar), 0.1 ml T-4 standard solution, and 15 mg of the microparticles of this example were prepared. The T-4 standard solution employed in each mixture contained a different known level of T-4 in 8 percent T-4 free serum solution. The mixtures were reacted at 20°-25° C. for 15 minutes and the complexed microparticles magnetically separated from the mixtures by placing a magnet next to the test vessel and decanting the reaction solution. Each of the samples of separated microparticles was then combined with 2 ml barbitol buffer solution (0.075 molar, pH 8.6) containing 1 percent human serum and tracer amounts of $^{125}I$-T-4 (1.0 mg, 150 μCi; or less) and the resulting mixtures reacted for 60 minutes at 20°-25° C. The particles were then magnetically separated from the serum and counted for radioactivity using a Model 1185 gamma counter available from Searle Analytic Inc. Results of the test are reported in Table I as % radioactivity sorbed by the microparticles as a function of the T-4 concentration in the standard solutions. This data was used to construct a standard curve.

TABLE I

| T-4 Standard Solution (μg/100 ml) | Radioactivity[1] Sorbed by Particles (cpm) | % Radioactivity Sorbed by Particles |
|---|---|---|
| 1.5 | 8228 | 39.2 |
| 3.0 | 9727 | 46.3 |
| 6.0 | 12206 | 58.1 |
| 12.0 | 14202 | 67.6 |
| 24.0 | 16198 | 77.1 |

[1]Total Radioactivity 21009 cpm

The T-4 content of separate unknown serum compositions was then determined from the above curve by using the magnetically responsive microparticles of this example and procedures described above by comparing the radioactivity sorbed by the microparticles used with the unknown sample with that sorbed by the microparticles used with the known samples. The radioassay of the unknown serum samples was run simultaneously with that of the known samples. The results of these tests are summarized in Table II.

TABLE II

| Serum Sample | Radioactivity Sorbed by Particles (cpm) | % Radioactivity Sorbed by Particles | T-4 in Serum Sample (μg/100 ml) |
|---|---|---|---|
| Pooled serum[a] | 12542 | 59.7 | 7.2 |
| "Ortho I"[b] | 12059 | 57.4 | 6.0 |
| "Ortho II"[c] | 14916 | 71.0 | 16.0 |

[a]Prepared by blending equal portions of serum from 5 or more people
[b]A pooled human serum available from Ortho Diagnostics which has a norma thyroxine level.
[c]A pooled human serum availabe from Ortho Diagnostics which has a high (e.g. hyper) thyroxine level.

EXAMPLE 2

Magnetically responsive composite particles having magnetically responsive material dispersed throughout a heat denatured, permeable, solid, water-insoluble protein matrix were prepared. An aqueous mixture comprising 0.5 g magnetically responsive material ($BaFe_{12}O_{19}$) in 1.5 ml protein (bovine serum albumin in water, 0.35 g/ml) was added dropwise to 3 liters of rapidly stirred cotton seed oil to produce a dispersion of the mixture in the oil. The dispersion was heated for 3 hours at about 120° to 130° C. to denature and dehydrate the protein matrix and provide water-insoluble particles. The particles were collected by vacuum filtration. Residual oil was removed from the particles by contacting the particles with n-heptane in a Soxhlet extractor for about 20 hours. Residual water-soluble components were then removed from the particles in a similar manner by contacting the particles with water in a Soxhlet extractor. The resulting particles were vacuum dried at 80° C. for 24 hours. The dried particles were spherical and approximately 90 percent had diameters in the range of about 10 to 250 microns.

A standard curve was then constructed by following the procedures described in Example 1. The results of these tests are summarized in Table III as the percentage radioactivity bound to particles as a function of the T-4 in the standard solutions.

TABLE III

| T-4 Standard Solution (μg/100 ml) | Radioactivity[1] Sorbed by Particles (cpm) | % Radioactivity Sorbed by Particles |
|---|---|---|
| 1.5 | 8526 | 41.0 |
| 3.0 | 9811 | 47.2 |
| 6.0 | 11996 | 57.7 |
| 12.0 | 14200 | 68.3 |
| 24.0 | 15897 | 76.4 |

[1]Total Radioactivity 20801 cpm

The T-4 content of unknown serum samples was determined as described in Example 1 using the microparticles and assay procedures of this example. The unknown samples were assayed simultaneously with the known samples. The results of these tests are summarized in Table IV.

TABLE IV

| Serum Sample | Radioactivity Sorbed by Particles (cpm) | % Radioactivity Sorbed by Particles | T-4 in Serum Sample (μg/100 ml) |
|---|---|---|---|
| Pooled Serum | 12221 | 58.7 | 7.0 |
| "Ortho I" | 10686 | 51.4 | 4.4 |
| "Ortho II" | 14731 | 70.8 | 16.0 |

EXAMPLE 3

Magnetically responsive composite particles having magnetically responsive material and a non-proteinaceous sorbent dispersed throughout a permeable, solid, crosslinked, water-insoluble protein matrix were prepared according to the procedures described in Example 1. The aqueous mixture comprised 1.3 g magnetically responsive material ($BaFe_{12}O_{19}$), 2.6 g non-proteinaceous sorbent (granulated charcoal) and 1.5 ml protein solution (bovine serum albumin in water, 0.35 gm/ml). The continuous phase comprised 500 ml dewatering agent (n-butanol), 20 ml crosslinking agent (formaldehyde, 35 percent by weight in water), and 500 ml oil (castor oil). The resulting magnetically responsive particles were spherical and approximately 90 percent had diameters in the range of from about 40 to 400 microns.

These particles were used in a vitamin $B_{12}$ radioassay as follows:

Separate mixtures each comprising 1 ml glycine - HCl buffer (0.5 pH 3.4), 0.2 ml $^{57}$Co-$B_{12}$ (100 pg/ml, 25 nCi/ml or less), 0.2 ml potassium cyanide (200 µg/ml), and 0.2 ml $B_{12}$ standard solutions. The $B_{12}$ standard solutions in each mixture contained a different known level of vitamin $B_{12}$. The mixtures were heated at 100° C. for 15 minutes and then cooled to room temperature (e.g., 20°–25° C.). One milliliter of a glycine-NaOH buffer (0.2 molar, pH 9.6) and 0.2 ml diluted oyster toadfish serum (1:8000 v/v dilution in phosphate buffer, 0.05 molar, pH 7.2) were added. The resultant mixture was reacted for 30 minutes at room temperature. After the reaction 50 mg of the magnetically responsive microparticles of this example were added. The resultant mixture was reacted for 15 minutes at room temperature and the complexed magnetically responsive microparticles separated from the mixture and the remaining liquid portion counted for radioactivity as described in Example 1. The results of these tests, summarized in Table V were used to construct a standard curve.

TABLE V

| $B_{12}$ Standard Solutions (pg/m/l) | Radioactivity Bound to Toadfish Serum (cpm) | $\left(\dfrac{B_x}{B_o}\right)100$ |
| --- | --- | --- |
| 0 | 2825 | 100.0 |
| 25 | 2748 | 97.3 |
| 50 | 2588 | 91.6 |
| 100 | 2401 | 85.0 |
| 200 | 2147 | 76.0 |
| 400 | 1667 | 59.0 |
| 800 | 1328 | 47.0 |
| 1600 | 618 | 21.9 |

$B_x$ = radioactivity bound to toadfish serum proteins in standard solutions
$B_o$ = radioactivity bound to toadfish serum proteins in zero standard solution The vitamin $B_{12}$ content of human pooled serum samples (e.g., serum prepared by blending equal portions of serum from five or more people) was determined using the microparticles and assay procedures of this example from the standard curve as described in Example 1. The pooled serum samples and the standards were assayed simultaneously. The results of this test show that the pooled serum contained 560 pg $B_{12}$/100 ml endogenous vitamin $B_{12}$.

EXAMPLE 4

Magnetically responsive composite particles were prepared using the procedures described in Example 3 and substituting an anion exchange resin ("Amberlite 400", commercially available from Rohm and Haas) for the charcoal.

The aqueous mixture comprised 5.0 g magnetically responsive material ($BaFe_{12}O_{19}$), 1.0 g anion exchange resin and 3.3 ml protein solution (bovine serum albumin in water, 0.3 g/ml). The continuous phase comprised 250 ml dewatering agent (n-butanol), 10 ml crosslinking agent (formaldehyde, 35 percent by weight in water) and 250 ml oil (castor oil). The magnetically responsive particles were spherical and approximately 90 percent had diameters in the range of about 40 to 400 microns.

The ability of the anion-exchange resin in the composite microparticles of this example to sorb substances was demonstrated by incubating 100 mg of the microparticles at room temperature with 2 ml $^{99m}TcO_4^-$ (40 mCi tracer technetium). It was found that composite microparticles containing the anion-exchange resin in the matrix sorbed 99.5 percent of the technetium after 60 minutes incubation. On the other hand, composite microparticles containing no anion-exchange resin in the matrix did not sorb this radioactive material.

The microparticles of this example were then used to construct a sorption curve. One ml barbital buffer (pH 8.6) and 0.2 ml radiolabeled T-4 ($^{125}$I-T-4, 3.8 mg T-4/200 nCi/ml barbital buffer) and 0.5 ml of a solution of barbital buffer and 0.05 percent human serum albumin were combined and reacted for 30 minutes at room temperature. Individual portions of the resultant mixture were then combined with varying amounts of the microparticles of this example and incubated at room temperature for 30 minutes. The microparticles were then magnetically separated and counted for radioactivity. The quantity of microparticles used and the percent radioactivity sorbed by those microparticles are given in Table VI.

TABLE VI

| Quantity Microparticles | % Radioactivity Sorbed by Particles |
| --- | --- |
| 50 mg | 73.4 |
| 25 mg | 65.1 |
| 15 mg | 53.6 |

EXAMPLE 5

Magnetically responsive composite particles were prepared according to the procedure described in Example 1. An aqueous mixture (5 ml) comprising 1.5 g magnetically responsive material ($BaFe_{12}O_{19}$), 2 ml sockeye salmon serum and 3 ml bovine serum albumin (0.35 g/ml) was added dropwise into a rapidly stirred continuous phase comprising 500 ml dewatering agent (n-butanol), 20 ml crosslinking agent (formaldehyde, 35 percent by weight in water) and 500 ml oil (castor oil). The resultant particles were spherical and approximately 90 percent had diameters in the range of about 10 to 100 microns.

The microparticles were used in vitamin $B_{12}$ radioassays as follows:

Separate mixtures comprising 1.0 ml glycine-HCl buffer (0.5 molar, pH 3.4), 0.2 ml $^{57}$Co-$B_{12}$ (100 pg/100 ml), 0.2 ml potassium cyanide (200 µg/ml) and 0.2 ml $B_{12}$ standard solutions. The $B_{12}$ standard solutions in each mixture contained different known amounts of $B_{12}$. The samples were heated at 100° C. for 15 minutes and then cooled to room temperature. One milliliter of glycine-NaOH buffer (0.2 molar, pH 9.6) and 5 mg of the magnetically responsive particles of this example were added to each sample and allowed to react therewith for 60 minutes at room temperature. The magnetic particles were then magnetically separated and the remaining liquid portion counted for radioactivity. The results of these tests, summarized in Table VII were used to construct a standard curve.

TABLE VII

| Standard Solutions (pg/ml) | Radioactivity Bound to Particles (cpm) | $\left(\dfrac{B_x}{B_o}\right)100$ |
| --- | --- | --- |
| 0 | 3725 | 100.0 |
| 25 | 3654 | 98.1 |
| 50 | 3528 | 94.7 |
| 100 | 3215 | 86.3 |
| 200 | 2935 | 78.8 |
| 400 | 2243 | 60.2 |
| 800 | 1687 | 45.3 |
| 1600 | 1393 | 37.4 |

$B_x$ = radioactivity bound to particles in standards
$B_o$ = radioactivity bound to particles in zero standards The vitamin $B_{12}$ content of human pooled serum samples was determined using the magnetically responsive particles and assay procedure of this example. The pooled serum samples and the standards were assayed simultaneously. The results of this test show that the serum contains 660 pg $B_{12}$/100 ml endogenous vitamin $B_{12}$.

EXAMPLE 6

Magnetically responsive microparticles having magnetically responsive material dispersed throughout a permeable, solid, crosslinked water-insoluble polyurethane matrix were prepared. About 245 g "Formrez P611" [1] was mixed with 150 g magnetically responsive material ($BaFe_{12}O_{19}$) in 20 g of methylethylketone at 60° C. until a uniform mixture was obtained. Thirteen grams of a surfactant ("G 1300" from Atlas Chemical Company, a polyoxyethylene fatty glyceride) was also added to the mixture.

[1] An isocyanate-terminated polyester prepolymer formed by reacting 4,4'-diphenyl methane diisocyanate with a polyester (i.e., the ester reaction product of a glycol and a dicarboxylic acid). It is a waxy thermoplastic solid at room temperature and has an isocyanate equivalent weight of 627–667 and from about 5.8 to 6.4 of its weight as available isocyanate (NCO) groups. It is available from Witco Chemical Company.

The mixture was then extruded into a continuous water phase and was dispersed into small droplets by a mixer operating at about 6,000 rpm. Once the mixture was dispersed as droplets the mixer was slowed to 2,000–3,000 rpm and the dispersion heated to 80° C. for 20 minutes, during which time the isocyanate-terminated prepolymer was crosslinked and made water-insoluble. The microparticles were then screened, filtered and oven dried at about 60° C. Approximately 90 percent of the particles had diameters in the range of 5 to 75 microns.

The microparticles were then used to construct a standard curve. Two ml radiolabeled T-4 bound to thyroxine antibody ($^{125}$I-T-4 bound to α-globulin, 400 mg/100 ml) were added to separate T-4 standard solutions each containing a different amount of T-4. The solutions were counted for radioactivity after which 100 mg of the microparticles of this example were added. The mixture was then reacted at room temperature for 20 minutes. The particles were magnetically separated and counted for radioactivity. The results are given in Table VIII.

TABLE VIII

| T-4 Standard Solution (μg/100 ml) | % Radioactivity Sorbed by Particles |
| --- | --- |
| 2 | 10.9 |
| 5 | 22.5 |
| 10 | 36.3 |
| 15 | 41.4 |
| 18 | 47.2 |

What is claimed is:

1. A method for determining the concentration of substances present in biological fluids comprising the steps of:
   providing a mixture of (i) a known quantity of said biological fluid containing said substance whose concentration is to be determined, (ii) a known quantity of a radioactively labeled form of said substance and (iii) a known quantity of magnetically responsive composite microparticles comprising a magnetically responsive material and a permeable, solid, water-insoluble matrix selected from proteinaceous materials, polysaccharides, polyurethanes and mixtures thereof; wherein said magnetically responsive material is dispersed throughout said water-insoluble matrix; and wherein said water-insoluble matrix is capable of sorbing said substances;
   reacting said mixture so as to cause said substance and its radioactively labeled form to competitively complex with said composite microparticles;
   magnetically separating the complexed microparticles from the mixture;
   counting the radioactivity of either the separated complexes or the remaining mixture; and
   relating the counted radioactivity to a standard curve to determine the concentration of said substance.

2. A method in accordance with claim 1 wherein said water-insoluble matrix is a proteinaceous material.

3. A method in accordance with claim 2 wherein said proteinaceous material is selected from albumins, gelatin, globulins and enzymes.

4. A method in accordance with claim 3 wherein said proteinaceous material is an albumin.

5. A method in accordance with claim 3 wherein said proteinaceous material is a globulin.

6. A method in accordance with claim 3 wherein said proteinaceous material is an enzyme.

7. A method in accordance with claim 3 wherein said proteinaceous material is gelatin.

8. A method in accordance with claim 1 wherein said water insoluble matrix is a polysaccharide.

9. A method in accordance with claim 1 wherein said magnetically responsive material is a ferromagnetic material.

10. A method in accordance with claim 9 wherein said ferromagnetic material is selected from $BaFe_{12}O_{19}$, $Fe_3O_4$, $CoO$, $NiO$, $Mn_2O_3$, $CoMnP$, iron particles and nickel particles.

11. A method in accordance with claim 1 wherein said composite microparticle has a maximum dimension in the range of about 5 to 400 microns.

12. A method in accordance with claim 1 wherein there is further included in said permeable, solid, water-insoluble matrix a combining agent capable of sorbing substances present in biological fluids, wherein said combining agent is selected from activated charcoal, ion-exchange resins, and binding agents which have a specific affinity for said substance.

13. A method in accordance with claim 12 wherein said combining agent is activated charcoal.

14. A method in accordance with claim 12 wherein said combining agent is an ion-exchange resin.

15. A method in accordance with claim 14 wherein said ion-exchange resin contains fixed electronegative charges.

16. A method in accordance with claim 14 wherein said ion-exchange resin contains fixed electropositive charges.

17. A method in accordance with claim 12 wherein said combining agent is a binding agent which has a specific affinity for said substances.

18. A method in accordance with claim 17 wherein said binding agent is a protein.

19. A method in accordance with claim 18 wherein said binding protein is selected from thyroxine antibody, intrinsic factor and fish serum.

20. A method in accordance with claim 1 wherein said substance is thyroxine.

21. A method in accordance with claim 1 wherein said substance is vitamin $B_{12}$.

22. A method in accordance with claim 1 wherein said water-insoluble matrix is a polyurethane.

23. A method in accordance with claim 22 wherein said polyurethane is the reaction product of a polyisocyanate and a material having reactive hydroxyl groups, said material being selected from polyols, polyesters and polyethers.

24. A method in accordance with claim 22 wherein said polyurethane is prepared by reacting an isocyanate-terminated polyester prepolymer.

25. A method in accordance with claim 24 wherein said prepolymer is prepared by reacting 4,4'-diphenyl methane diisocyanate with the reaction product of a glycol and a dicarboxylic acid.

* * * * *

UNITED STATES PATENT AND TRADEMARK OFFICE
CERTIFICATE OF CORRECTION

PATENT NO. : 4,115,534

DATED : September 19, 1978

INVENTOR(S) : DIONYSSIS S. ITHAKISSIOS

It is certified that error appears in the above-identified patent and that said Letters Patent are hereby corrected as shown below:

Col. 9, line 17, "are" should read -- were --.

Col. 11, line 45, "(pg/m/1)" should read -- (pg/ml) --.

Col. 13, line 10, "Standard Solutions" should read --
$B_{12}$ Standard Solutions (pg/ml) --.

*Signed and Sealed this*

*Twentieth* Day of *March 1979*

[SEAL]

Attest:

RUTH C. MASON
*Attesting Officer*

DONALD W. BANNER
*Commissioner of Patents and Trademarks*